US012714391B2

(12) United States Patent
Uemura et al.

(10) Patent No.: US 12,714,391 B2
(45) Date of Patent: Aug. 25, 2026

(54) ULTRASONIC TONOMETER AND NON-TRANSITORY COMPUTER READABLE STORAGE MEDIUM

(71) Applicant: NIDEK CO., LTD., Gamagori (JP)

(72) Inventors: Tsutomu Uemura, Gamagori (JP); Kazunari Shimizu, Gamagori (JP); Koji Hamaguchi, Gamagori (JP)

(73) Assignee: NIDEK CO., LTD., Gamagori (JP)

( * ) Notice: Subject to any disclaimer, the term of this patent is extended or adjusted under 35 U.S.C. 154(b) by 327 days.

(21) Appl. No.: 18/477,861

(22) Filed: Sep. 29, 2023

(65) Prior Publication Data

US 2024/0016472 A1 Jan. 18, 2024

Related U.S. Application Data

(63) Continuation of application No. PCT/JP2022/012555, filed on Mar. 18, 2022.

(30) Foreign Application Priority Data

Mar. 31, 2021 (JP) ................................ 2021-061913
Mar. 31, 2021 (JP) ................................ 2021-061914

(51) Int. Cl.
*A61B 8/10* (2006.01)
*A61B 3/16* (2006.01)

(52) U.S. Cl.
CPC ................ *A61B 8/10* (2013.01); *A61B 3/165* (2013.01)

(58) Field of Classification Search
CPC ......... A61B 8/10; A61B 3/165; A61B 3/0008; A61B 3/0083; A61B 3/152
USPC ........................................................ 351/208
See application file for complete search history.

(56) References Cited

U.S. PATENT DOCUMENTS

| | | | |
|---|---|---|---|
| 5,396,888 | A | 3/1995 | Massie et al. |
| 5,636,635 | A | 6/1997 | Massie et al. |
| 5,865,742 | A | 2/1999 | Massie |
| RE45,013 | E | 7/2014 | Miwa |

(Continued)

FOREIGN PATENT DOCUMENTS

| | | | |
|---|---|---|---|
| JP | 5-253190 | A | 10/1993 |
| JP | 2009-268651 | A | 11/2009 |

(Continued)

OTHER PUBLICATIONS

International Search Report (PCT/ISA/210) issued Jun. 14, 2022 by the International Searching Authority in counterpart International Patent Application No. PCT/JP2022/012555.

(Continued)

*Primary Examiner* — William R Alexander
(74) *Attorney, Agent, or Firm* — Sughrue Mion, PLLC

(57) ABSTRACT

An ultrasonic tonometer for measuring intraocular pressure of a subject eye by using an ultrasonic wave. The ultrasonic tonometer includes an irradiation unit configured to irradiate the subject eye with a focused ultrasonic wave, and a Z-alignment detection unit configured to detect an alignment state in a working distance direction with respect to the subject eye. An appropriate Z-alignment position is set to a position that is farther from the irradiation unit than is a geometric focal position of the irradiation unit. The appropriate Z-alignment position is detected by the Z-alignment detection unit.

22 Claims, 7 Drawing Sheets

(56) References Cited

U.S. PATENT DOCUMENTS

| | | | | |
|---|---|---|---|---|
| 2004/0054277 | A1* | 3/2004 | Uchida | A61B 3/165 600/399 |
| 2009/0030299 | A1* | 1/2009 | Naito | A61B 3/165 600/399 |
| 2009/0275819 | A1 | 11/2009 | Miwa | |
| 2009/0275820 | A1 | 11/2009 | Miwa | |
| 2014/0092361 | A1* | 4/2014 | Takii | A61B 3/1005 351/205 |
| 2019/0133436 | A1 | 5/2019 | Arikawa et al. | |
| 2020/0077890 | A1* | 3/2020 | Bian | A61B 3/0083 |
| 2021/0068656 | A1 | 3/2021 | Miwa et al. | |

FOREIGN PATENT DOCUMENTS

| | | | |
|---|---|---|---|
| JP | 2009-291595 | A | 12/2009 |
| JP | 2010-68873 | A | 4/2010 |
| JP | 2015-85042 | A | 5/2015 |
| JP | 2017-196305 | A | 11/2017 |
| JP | 2019-177034 | A | 10/2019 |

OTHER PUBLICATIONS

Written Opinion (PCT/ISA/237) issued Jun. 14, 2022 by the International Searching Authority in counterpart International Patent Application No. PCT/JP2022/012555.

* cited by examiner 200
220
222
221
202
500
231
232
234
O1
230
201
233
O2
210
101
400
100
280
260
261
282
204
262
281
263
265
O3
266
264
L1
260
241
O4
241
E
240

311
312
75
300
320
313
310 (330)
314

ULTRASONIC TONOMETER AND NON-TRANSITORY COMPUTER READABLE STORAGE MEDIUM

CROSS-REFERENCE TO RELATED APPLICATIONS

This is a continuation application of International Application No. PCT/JP2022/012555 filed on Mar. 18, 2022 which claims priority from Japanese Patent Application No. 2021-061913 filed on Mar. 31, 2021 and Japanese Patent Application No. 2021-061914 filed on Mar. 31, 2021. The entire contents of the earlier applications are incorporated herein by reference.

TECHNICAL FIELD

The present disclosure relates to an ultrasonic tonometer for measuring intraocular pressure of a subject eye by using an ultrasonic wave, and a non-transitory computer readable storage medium storing an ultrasonic tonometer control program.

BACKGROUND ART

As a non-contact type tonometer, an air injection type tonometer has generally been used so far. The air injection type tonometer converts an air pressure in a predetermined deformation state into intraocular pressure by detecting an applanation state of a cornea when air is injected into the cornea and the air pressure injected into the cornea.

In addition, as a non-contact type tonometer, an ultrasonic tonometer for measuring intraocular pressure by using an ultrasonic wave has been proposed (see JPH05-253190). The ultrasonic tonometer disclosed in JPH05-253190 converts radiation pressure in a predetermined deformation state into intraocular pressure by detecting an applanation state of a cornea when an ultrasonic wave is radiated to the cornea and the radiation pressure to be injected to the cornea.

Further, as an ultrasonic tonometer, a device that measures an intraocular pressure based on the relationship between the characteristics (amplitude and phase) of reflected waves from the cornea and the intraocular pressure has been proposed (see JP2009-268651).

As a first problem, in the ultrasonic tonometer as described above, in a case where the output of an ultrasonic wave increases, the focal position of the ultrasonic wave shifts, and there are cases where a subject eye cannot be appropriately irradiated with an ultrasonic wave.

As a second problem, in the ultrasonic tonometer as described above, the optical axis of an optical system for alignment detection and the sound axis of an ultrasonic irradiation unit may deviate due to variations in the characteristics of ultrasonic elements or assembly errors. In such a case, even in a case where an ultrasonic wave is optically aligned with respect to the subject eye, the focal position of the ultrasonic wave is shifted, and the subject eye cannot be appropriately irradiated with an ultrasonic wave.

SUMMARY OF INVENTION

Aspect of non-limiting embodiments of the present disclosure relates to provide an ultrasonic tonometer and a non-transitory computer readable storage medium storing an ultrasonic tonometer control program that can appropriately irradiate a subject eye with an ultrasonic wave.

Aspects of certain non-limiting embodiments of the present disclosure address the features discussed above and/or other features not described above. However, aspects of the non-limiting embodiments are not required to address the above features, and aspects of the non-limiting embodiments of the present disclosure may not address features described above.

According to an aspect of the present disclosure, there is provided an ultrasonic tonometer for measuring intraocular pressure of a subject eye by using an ultrasonic wave, the ultrasonic tonometer including:

- an irradiation unit configured to irradiate the subject eye with a focused ultrasonic wave; and
- a Z-alignment detection unit configured to detect an alignment state in a working distance direction with respect to the subject eye,
- in which an appropriate Z-alignment position is set to a position that is farther from the irradiation unit than is a geometric focal position of the irradiation unit, the appropriate Z-alignment position being detected by the Z-alignment detection unit.

According to an aspect of the present disclosure, there is provided a non-transitory computer readable storage medium storing an ultrasonic tonometer control program used in an ultrasonic tonometer for measuring intraocular pressure of a subject eye by using an ultrasonic wave, the ultrasonic tonometer control program including instructions which, when executed by a controller, cause the ultrasonic tonometer to perform:

- a Z-alignment detection step of detecting an alignment state in a working distance direction with respect to the subject eye; and
- a setting step of setting an appropriate Z-alignment position to a position that is farther from an irradiation unit than is a geometric focal position of the irradiation unit, the irradiation unit being configured to irradiate the subject eye with a focused ultrasonic wave, the appropriate Z-alignment position being detected in the Z-alignment detection step.

According to an aspect of the present disclosure, there is provided an ultrasonic tonometer for measuring intraocular pressure of a subject eye by using an ultrasonic wave, the ultrasonic tonometer including:

- an irradiation unit configured to irradiate the subject eye with an ultrasonic wave;
- an alignment detection unit including an imaging optical system configured to image an anterior chamber of the subject eye, the alignment detection unit being configured to detect an alignment state with respect to the subject eye, based on an anterior chamber image acquired by the imaging optical system; and
- a controller configured to correct alignment information acquired by the alignment detection unit, based on an amount of deviation between an optical axis of the imaging optical system and a sound axis of the irradiation unit.

According to an aspect of the present disclosure, there is provided a non-transitory computer readable storage medium storing an ultrasonic tonometer control program used in an ultrasonic tonometer for measuring intraocular pressure of a subject eye by using an ultrasonic wave, the ultrasonic tonometer control program including instructions which, when executed by a controller of the ultrasonic tonometer, cause the ultrasonic tonometer to perform:

- an alignment detection step of detecting an alignment state with respect to the subject eye, based on an anterior chamber image acquired by an imaging optical system configured to image an anterior chamber of the subject eye; and a correction step of correcting alignment information acquired in the alignment detection step, based on an amount of deviation between an optical axis of the imaging optical system and a sound axis of an irradiation unit.

BRIEF DESCRIPTION OF DRAWINGS

Exemplary embodiment(s) of the present invention will be described in detail based on the following figures, wherein.

DESCRIPTION OF EMBODIMENTS

First Embodiment

Figure 1:
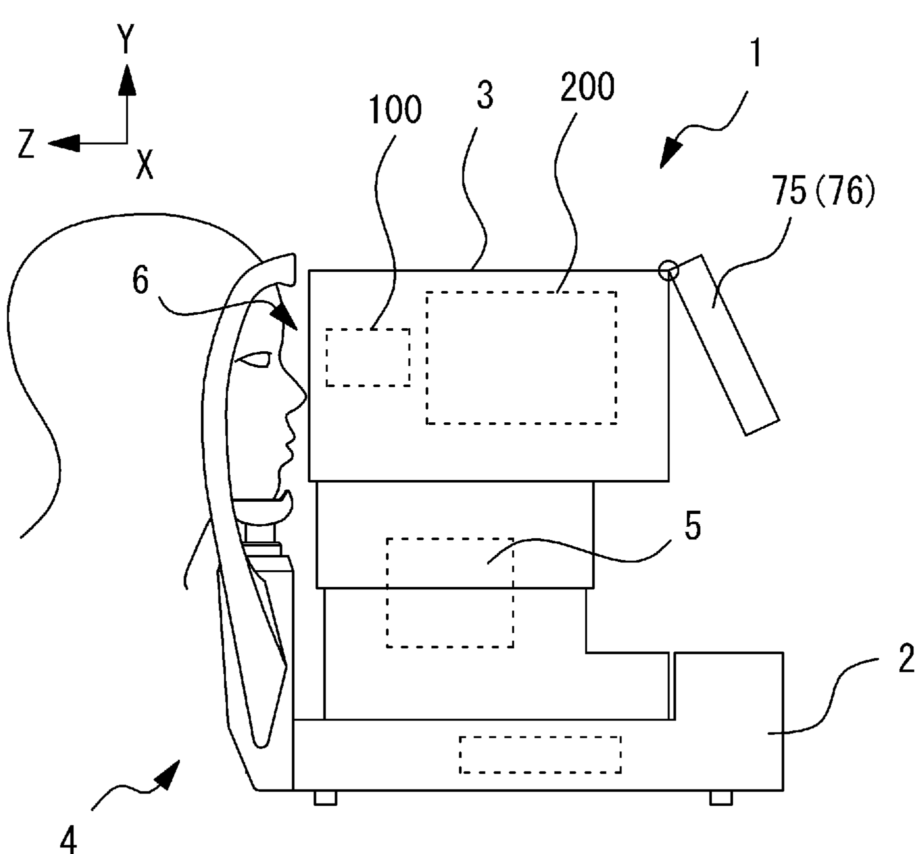
FIG. 1 is an external diagram of an ultrasonic tonometer.

A first embodiment according to the present disclosure will be described. An ultrasonic tonometer (for example, ultrasonic tonometer 1) of the present embodiment is configured to measure intraocular pressure of a subject eye by using an ultrasonic wave, for example. The ultrasonic tonometer includes, for example, an irradiation unit (for example, irradiation unit 100), an alignment detection unit (for example, optical system 200), and a controller (for example, controller 70). The irradiation unit, for example, is configured to irradiate a subject eye with an ultrasonic wave. The alignment detection unit includes an imaging optical system (for example, observation system 220) configured to image the anterior chamber of the subject eye, and configured to detect the alignment state with respect to the subject eye, based on an anterior chamber image acquired by the imaging optical system. For example, based on the amount of deviation (for example, the amount of deviation in the vertical and horizontal directions) between the optical axis of the imaging optical system (for example, optical axis O1) and the sound axis of the irradiation unit (for example, sound axis L1), the controller is configured to correct the alignment information acquired by the alignment detection unit. As a result, the ultrasonic tonometer of a first embodiment can appropriately irradiate the subject eye with an ultrasonic wave.

The sound axis is, for example, the central axis of the ultrasonic wave to be applied by the irradiation unit. The sound axis extends, for example, in the traveling direction of the ultrasonic wave or the oscillation direction of the irradiation unit, and passes through the focal position where the ultrasonic wave output by the irradiation unit is focused. For example, the controller may be configured to correct the alignment information, based on the amount of deviation in the vertical and horizontal directions (XY directions) between the optical axis of the imaging optical system and the focal position of the irradiation unit. In addition, the controller may be configured to correct alignment information, based on the amount of deviation (for example, the amount of deviation in the vertical, horizontal, front-rear directions) between the detection reference position of the alignment detection unit (for example, the focal position of the imaging optical system) and the focal position of the irradiation unit.

The ultrasonic tonometer may further include a measurement optical system (for example, measurement optical system 500) that shares an optical axis with the imaging optical system, and configured to measure an eye characteristic different from intraocular pressure. In this case, the controller may be configured to switch whether or not to correct the alignment information between the measurement of the eye characteristic by the measurement optical system and the measurement of the intraocular pressure by the irradiation unit. For example, the controller may be configured not to correct the alignment information when measuring the eye characteristics by the measurement optical system, and may be configured to correct the alignment information, based on the amount of deviation between the optical axis and the sound axis, when measuring the intraocular pressure by the irradiation unit. As a result, an ultrasonic wave can be appropriately radiated during intraocular pressure measurement, and the eye characteristic can be suitably measured by the measurement optical system.

The ultrasonic tonometer may further include a drive unit (for example, drive unit configured to move the irradiation unit. In this case, the controller may be configured to control the drive unit, based on the alignment information corrected by the controller to align the irradiation unit with respect to the subject eye. As a result, the ultrasonic tonometer can automatically align the irradiation unit with respect to the subject eye.

The controller may be configured to cause a display (for example, display 75) to display the alignment information corrected by the controller. In this case, an examiner can operate an operation unit (for example, operation unit 76) while checking the alignment information displayed on the display to manually and appropriately align the irradiation unit with respect to the subject eye.

The controller may be configured to correct the alignment information, according to the resonance frequency of the irradiation unit. For example, the amount of deviation between the optical axis of the imaging optical system and the sound axis of the irradiation unit may be stored in a storage unit or the like for each resonance frequency of the irradiation unit, to correct the alignment information based on the amount of deviation corresponding to the resonance frequency of the irradiation unit. This makes it possible to perform suitable alignment in consideration of changes in the sound axis according to the resonance frequency of the irradiation unit.

The controller may be configured to execute an ultrasonic tonometer control program stored in a storage unit or the like. The ultrasonic tonometer control program includes, for example, an alignment detection step and a correction step.

The alignment detection step is, for example, a step of detecting an alignment state with respect to the subject eye, based on an anterior chamber image acquired by the imaging optical system configured to image the anterior chamber of the subject eye. The correction step is, for example, a step of correcting the alignment information acquired in the alignment detection step, based on the amount of deviation between the optical axis of the imaging optical system and the sound axis of the irradiation unit.

Second Embodiment

A second embodiment according to the present disclosure will be described. The ultrasonic tonometer (for example, ultrasonic tonometer 1) of the second embodiment includes an irradiation unit (for example, irradiation unit 100) and a Z-alignment detection unit (for example, Z-alignment detection system 280). The irradiation unit is configured to irradiate the subject eye with a focused ultrasonic wave. The Z-alignment detection unit is configured to detect the alignment state of the subject eye in a working distance direction (front-rear direction or Z direction). In the second embodiment, an appropriate Z-alignment position to be detected by the Z-alignment detection unit is set farther in the working distance direction than the geometric (shape) focal position of the irradiation unit. As a result, the ultrasonic tonometer of the second embodiment can perform alignment in consideration of the focal position shift of the irradiation unit due to the increase in sound pressure, and can appropriately irradiate the subject eye with an ultrasonic wave.

The appropriate Z-alignment position may be set according to the arrangement relationship between the Z-alignment detection unit and the irradiation unit, or may be set by changing the detection reference position of the Z-alignment detection unit. The detection reference position of the Z-alignment detection unit may be, for example, the focal position of a Z-alignment detection system or a position at a predetermined distance away from the focal position of the Z-alignment detection system.

The ultrasonic tonometer may further include a deformation detection unit (for example, deformation detection system 260) configured to detect the deformation state of the cornea of the subject eye. In this case, the detection position of the deformation detection unit may be set farther than the appropriate Z-alignment position. As a result, the deformation detection unit has a high detection sensitivity in a case where the cornea of the subject eye is pushed in, and it becomes easier to detect that the cornea is deformed into a predetermined shape.

The ultrasonic tonometer may further include a controller (for example, controller 70) configured to control the Z-alignment detection unit. The controller may be configured to change the appropriate Z-alignment position, according to the magnitude of the acoustic radiation pressure or the sound pressure of the focused ultrasonic wave irradiated by the irradiation unit. In addition, the controller may be configured to change the appropriate Z-alignment position according to the resonance frequency of the irradiation unit. In this way, the controller is configured to change the appropriate Z-alignment position, according to the output of the irradiation unit, thereby performing suitable alignment corresponding to the changes in the focal position of the ultrasonic wave that changes according to the output of the irradiation unit.

The controller may be configured to execute an ultrasonic tonometer control program stored in a storage unit or the like. The ultrasonic tonometer control program includes a Z-alignment detection step and a setting step. The Z-alignment detection step is, for example, a step of detecting the alignment state in the working distance direction with respect to the subject eye. The setting step is a setting step of setting the appropriate Z-alignment position detected in the Z-alignment detection step to be farther than the geometric focal position of the irradiation unit configured to irradiate the subject eye with a focused ultrasonic wave.

Example

Hereinafter, an example according to the present disclosure will be described. For example, the ultrasonic tonometer of the present example is configured to measure intraocular pressure of a subject eye by using an ultrasonic wave in a non-contact manner. For example, the ultrasonic tonometer is configured to optically or acoustically detect a shape change or an oscillation of the subject eye in a case where the subject eye is irradiated with the ultrasonic wave to measure the intraocular pressure. For example, the ultrasonic tonometer is configured to continuously irradiate the cornea with a pulse wave or a burst wave, and is configured to calculate the intraocular pressure based on the output information of the ultrasonic wave in a case where the cornea is deformed into a predetermined shape (for example, applanation state or flattened state). For example, the output information is the sound pressure of an ultrasonic wave, acoustic radiation pressure, an irradiation time (for example, elapsed time after a trigger signal is input), a frequency, or the like. For example, in a case where the cornea of the subject eye is deformed, the sound pressure of the ultrasonic wave, the acoustic radiation pressure, or an acoustic flow is used.

FIG. 1 shows the appearance of the device. An ultrasonic tonometer 1 includes, for example, a base 2, a housing 3, a face support unit 4, a drive unit 5, and the like. Inside the housing 3, an irradiation unit 100, an optical system 200, and the like, which will be described later, are disposed. The face support unit 4 is configured to support the face of a subject eye. For example, the face support unit 4 is installed on the base 2. For example, the drive unit 5 is configured to move the housing 3 with respect to the base 2 for alignment.

Figure 2:
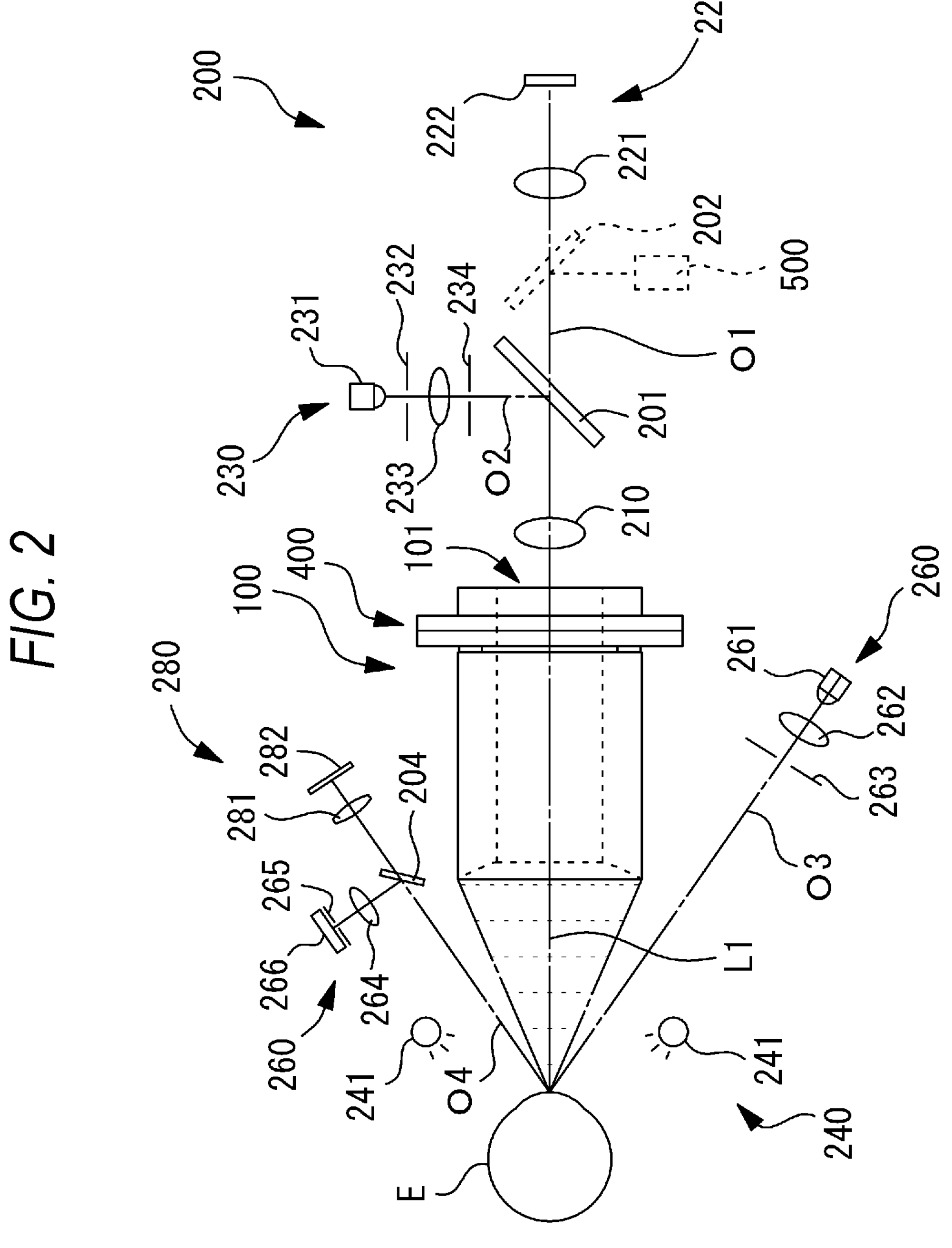
FIG. 2 is a schematic diagram showing the inside of a housing.

FIG. 2 is a schematic diagram of the main configuration inside the housing. For example, the irradiation unit 100 and the optical system 200 are disposed inside the housing 3. The irradiation unit 100 and the optical system 200 will be described in order with reference to FIG. 2.

<Irradiation Unit>

The irradiation unit 100 is configured to irradiate a subject eye E with ultrasonic waves, for example. For example, the irradiation unit 100 is configured to irradiate the cornea with an ultrasonic wave to generate acoustic radiation pressure within the cornea. For example, the acoustic radiation pressure is a force acting in a traveling direction of a sound wave. For example, the ultrasonic tonometer 1 of the present example is configured to use the acoustic radiation pressure to deform the cornea. The irradiation unit 100 of the present example has a cylindrical shape, and an optical axis O1 of the optical system 200, which will be described later, is disposed in a central opening 101 of the irradiation unit 100. The opening 101 is opened, for example, in the direction of the sound axis. A sound axis L1 is, for example, the central axis of the ultrasonic wave to be applied by the irradiation unit 100. The sound axis L1 is an axis extending in the traveling direction of an ultrasonic wave, the oscillation direction of the irradiation unit 100, or the like. The sound axis L1 passes through the focal position where the ultrasonic wave output by the irradiation unit 100 is focused. In the present example, the optical axis O1 of the optical system 200 and the sound axis L1 of the irradiation unit 100 are substantially coaxial.

Figures 3A, 3B:
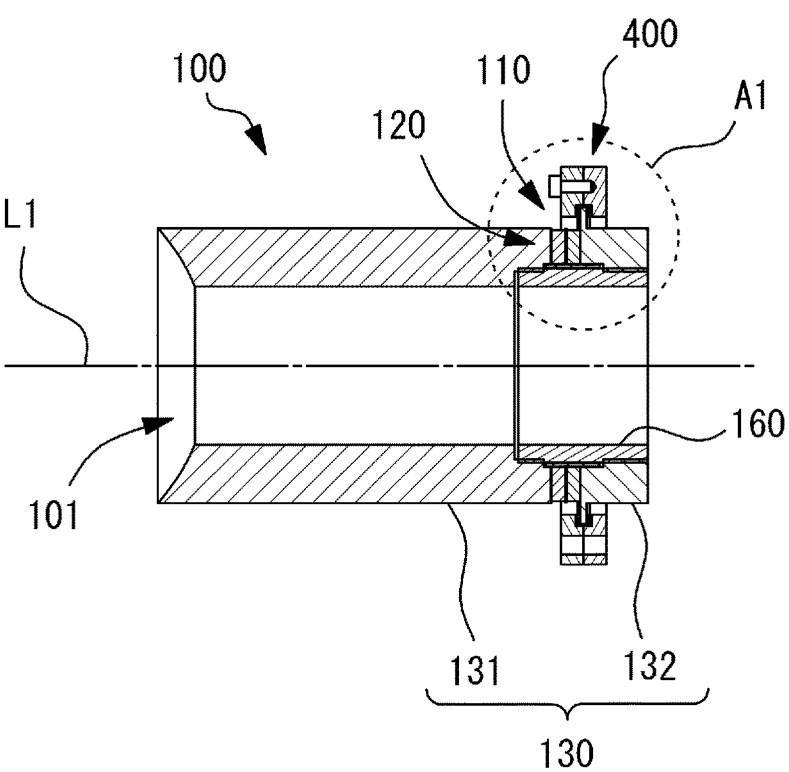
FIG. 3A is a schematic diagram showing the configuration of an irradiation unit.
FIG. 3B is a schematic diagram showing the configuration of the irradiation unit.

FIG. 3A is a cross-sectional diagram showing the schematic configuration of the irradiation unit 100, and FIG. 3B is the enlarged diagram of a range A1 shown in FIG. 3A. The irradiation unit 100 of the present example is a so-called Langevin oscillator. The irradiation unit 100 includes, for example, an ultrasonic element 110, an electrode 120, a mass member 130, a tightening member 160, and the like. The ultrasonic element 110 is configured to generate an ultrasonic wave. The ultrasonic element 110 may be a piezoelectric element (for example, piezoelectric ceramics) or a magnetostrictive element. The ultrasonic element 110 of the present example has a ring shape. For example, the ultrasonic element 110 may be formed by stacking a plurality of piezoelectric elements. In the present example, as the ultrasonic element 110, two stacked piezoelectric elements (for example, the piezoelectric element 111 and the piezoelectric element 112) are used. For example, respective electrodes 120 (electrode 121 and electrode 122) are connected to the two piezoelectric elements. For example, the electrode 121 and the electrode 122 of the present example have a ring shape.

For example, the mass member 130 pinches the ultrasonic element 110. For example, the mass member 130 pinches the ultrasonic element 110 to increase tensile strength of the ultrasonic element 110, and the ultrasonic element 110 can withstand a strong oscillation. In this manner, it is possible to generate a high-power ultrasonic wave. For example, the mass member 130 may be a metal block. For example, the mass member 130 includes a sonotrode (also referred to as a horn or a front mass) 131 and a back mass 132.

The sonotrode 131 is a mass member disposed in front of the ultrasonic element 110 (on the subject eye side). The sonotrode 131 is configured to propagate, into the air, the ultrasonic wave generated by the ultrasonic element 110. The sonotrode 131 of the present example has a cylindrical shape. A female screw portion 133 is formed in a part of the inner circular portion of the sonotrode 131. The female screw portion 133 is screwed to a male screw portion 161 formed in the tightening member 160 to be described later. The sonotrode 131 has a shape that focuses an ultrasonic wave. For example, the end surface of the sonotrode 131 on the side of the subject eye has a spherical shape focused on the sound axis L1. In addition, the sonotrode 131 may be a cylinder with a non-uniform thickness. For example, the sonotrode 131 may have a shape in which the outer diameter and the inner diameter change in the longitudinal direction of the cylinder.

The back mass 132 is a mass member disposed on a rear side of the ultrasonic element 110. The back mass 132 pinches the ultrasonic element 110 together with the sonotrode 131. For example, the back mass 132 has a cylindrical shape. The inner circular portion of the back mass 132 is partially formed with a female screw portion 134. The female screw portion 134 is screwed to the male screw portion 161 of the tightening member 160 to be described later. In addition, the back mass 132 includes a flange portion 135. The flange portion 135 is held by a mounting portion 400.

For example, the tightening member 160 tightens the mass member 130 and the ultrasonic element 110 pinched by the mass members 130. For example, the tightening member 160 is a hollow bolt. For example, the tightening member 160 has a cylindrical shape, and includes the male screw portion 161 on the outer circular portion. The male screw portion 161 of the tightening member 160 is screwed to the female screw portions 133 and 134 formed inside the sonotrode 131 and the back mass 132. The sonotrode 131 and the back mass 132 are tightened in a direction in which both attract each other by the tightening member 160. As a result, the ultrasonic element 110 sandwiched between the sonotrode 131 and the back mass 132 is tightened and pressure is applied.

The irradiation unit 100 may include an insulating member 170. For example, the insulating member 170 is configured to prevent the electrode 120 or the ultrasonic element 110 from coming into contact with the tightening member 160. For example, the insulating member 170 is disposed between the electrode 120 and the tightening member 160. For example, the insulating member 170 has a sleeve shape.

<Optical System>

For example, the optical system 200 is configured to observe or measure the subject eye (see FIG. 2). The optical system 200 includes, for example, an objective system 210, an observation system 220, a fixation target projection system 230, a deformation detection system 260, a dichroic mirror 201, a beam splitter 204, and the like.

The objective system 210 is, for example, an optical system configured to introduce light from outside the housing 3 into the optical system 200 or configured to irradiate the outside of the housing 3 with the light from the optical system 200. For example, the objective system 210 includes an optical element. The objective system 210 may include an optical element such as an objective lens, a relay lens, and the like.

An illumination system 240 is configured to illuminate the subject eye. For example, the illumination system 240 is configured to illuminate the subject eye with infrared light. For example, the illumination system 240 includes an illumination light source 241. For example, the illumination light source 241 is diagonally disposed in front of the subject eye. For example, the illumination light source 241 is configured to emit infrared light. The illumination system 240 may include a plurality of the illumination light sources 241.

For example, the observation system 220 is configured to capture an observation image of the subject eye. For example, the observation system 220 is configured to capture an image of the anterior chamber of the subject eye. The observation system 220 includes, for example, a light receiving lens 221, a light receiving element 222, and the like. For example, the observation system 220 is configured to receive, for example, light from the illumination light source 241 reflected by the subject eye. The observation system 220 is configured to receive, for example, a reflected light flux, from the subject eye, about the optical axis O1. For example, reflected light from the subject eye passes through the opening 101 of the irradiation unit 100 and is received by the light receiving element 222 via the objective system 210 and the light receiving lens 221. The corneal reflected bright spot of the illumination light source 241 received by the light receiving element 222 is used for vertical and horizontal alignment (XY alignment), for example. In this case, for example, the illumination system 240 and the observation system 220 is configured to function as XY alignment detection unit. Of course, apart from the illumination system 240, an index projection system configured to project, from the optical axis O1 onto the subject eye, an index for XY alignment may be provided. In this case, since a corneal center bright spot appears in the observation image of the observation system 220, the XY alignment may be performed based on this corneal center bright spot.

For example, the fixation target projection system 230 is configured to project a fixation target onto the subject eye. For example, the fixation target projection system 230 includes a target light source 231, a diaphragm 232, a light projection lens 233, a diaphragm 234, and the like. The light from the target light source 231 passes through the diaphragm 232, the light projection lens 233, the diaphragm 232, and the like along an optical axis O2, and is reflected by the dichroic mirror 201. For example, the dichroic mirror 201 is configured to causes the optical axis O2 of the fixation target projection system 230 to be coaxial with the optical axis O1. The light from the target light source 231 reflected by the dichroic mirror 201 passes through the objective system 210 along the optical axis O1, and is emitted to irradiate the subject eye. A target of the fixation target projection system 230 is fixated by a subject. Accordingly, a line of sight of the subject is stabilized.

The deformation detection system 260 is configured to detect, for example, deformation of the cornea of the subject eye. The deformation detection system 260 includes, for example, a light source 261, a light projection lens 262, a diaphragm 263, a light receiving lens 264, a diaphragm 265, a light receiving element 266, and the like. The light from the light source 261 passes through, for example, the light projection lens 262 and the diaphragm 263 along an optical axis O3, and is emitted to the subject eye. The light reflected by the subject eye is reflected by the beam splitter 204 along an optical axis O4, passes through the light receiving lens 264 and the diaphragm 265, and is received by the light receiving element 266. The deformation detection system 260 may be configured to detect deformation of the cornea, for example, based on the corneal reflected light received by the light receiving element 266.

The deformation detection system 260 may be configured to detect the deformation state of the cornea, based on the magnitude of the light receiving signal of the light receiving element 266, for example. For example, the deformation detection system 260 may be configured to detect that the cornea is in an applanation state in a case where the amount of light received by the light receiving element 266 becomes the maximum. In this case, for example, the deformation detection system 260 is set such that the amount of light received becomes maximum in a case where the cornea of the subject eye is in an applanation state.

The deformation detection system 260 may be an anterior chamber cross-sectional imaging unit such as an OCT or Scheimpflug camera. For example, the deformation detection system 260 may be configured to detect the amount or speed of deformation of the cornea.

A Z-alignment detection system 280 is configured to detect, for example, the alignment state in the Z direction. The Z-alignment detection system 280 includes a light receiving lens 281 and a light receiving element 282, for example. The Z-alignment detection system 280 may be configured to detect reflected light from the cornea to detect the alignment state in the Z direction, for example. For example, the Z-alignment detection system may be configured to receive light reflected by the cornea of the subject eye from the light source 261. In this case, the Z-alignment detection system 280 may be configured to receive, for example, a bright spot formed by the light from the light source 261 being reflected by the cornea of the subject eye. Thus, the light source 261 may also be used as a light source for Z-alignment detection.

For example, the light from the light source 261 reflected by the cornea passes through the beam splitter 204 and the light receiving lens 281 along the optical axis O4 and is received by the light receiving element 282. In a case where the subject eye and the Z-alignment detection system 280 deviate in the Z direction, the light receiving position of the light from the light source 261 reflected by the cornea (for example, the position where the light receiving signal has the maximum strength) deviates on the light receiving element 282. Therefore, the Z-alignment detection system 280 may be configured to detect the alignment state, based on the light receiving position of the light from the light source 261 on the light receiving element 282. For example, the Z-alignment detection system 280 is configured to detect whether or not the light receiving position of the light from the light source 261 is a predetermined pixel (detection reference position) of the light receiving element 282, or configured to detect how many pixels is deviated from the predetermined pixel, detect the alignment state.

<Controller>

Figure 4:
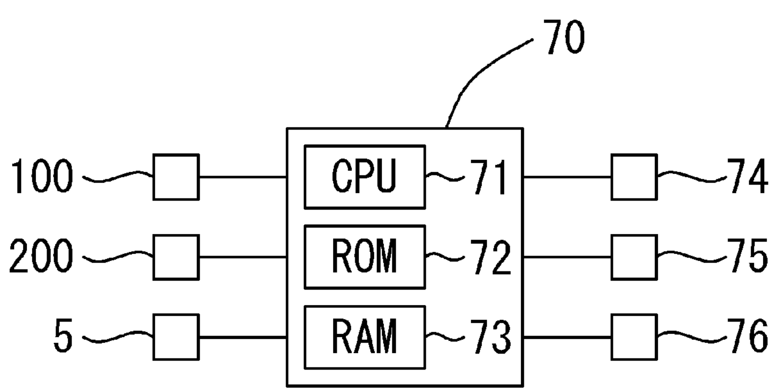
FIG. 4 is a block diagram showing a control system.

Next, a configuration of a control system will be described with reference to FIG. 4. For example, a controller 70 is configured to control the whole device, and is configured to perform arithmetic processing for measurement values. For example, the controller 70 includes a general central processing unit (CPU) 71, a ROM 72, a RAM 73, and the like. The ROM 72 is configured to store various programs or initial values for controlling an operation of the ultrasonic tonometer 1. The RAM 73 is configured to temporarily store various types of information. The controller 70 may include a single controller or a plurality of controllers (that is, a plurality of processors). The controller 70 may be connected to, for example, the drive unit 5, a storage unit 74, a display 75, an operation unit 76, the irradiation unit 100, the optical system 200, and the like.

The storage unit 74 is a non-transitory storage medium configured to hold stored content even in a case where power supply is interrupted. For example, a hard disk drive, a flash ROM, or a detachable USB memory can be used as the storage unit 74.

For example, the display 75 is configured to display a measurement result of the subject eye. The display 75 may have a touch panel function.

The operation unit 76 is configured to receive various operation instructions from an examiner. The operation unit 76 is configured to output, to the controller 70, an operation signal corresponding to the input operation instruction. For example, as the operation unit 76, at least one user interface such as a touch panel, a mouse, a joystick, and a keyboard may be used. In a case where the display 75 is a touch panel, the display 75 may be configured to function as the operation unit 76.

<Control Operation>

Figure 5:
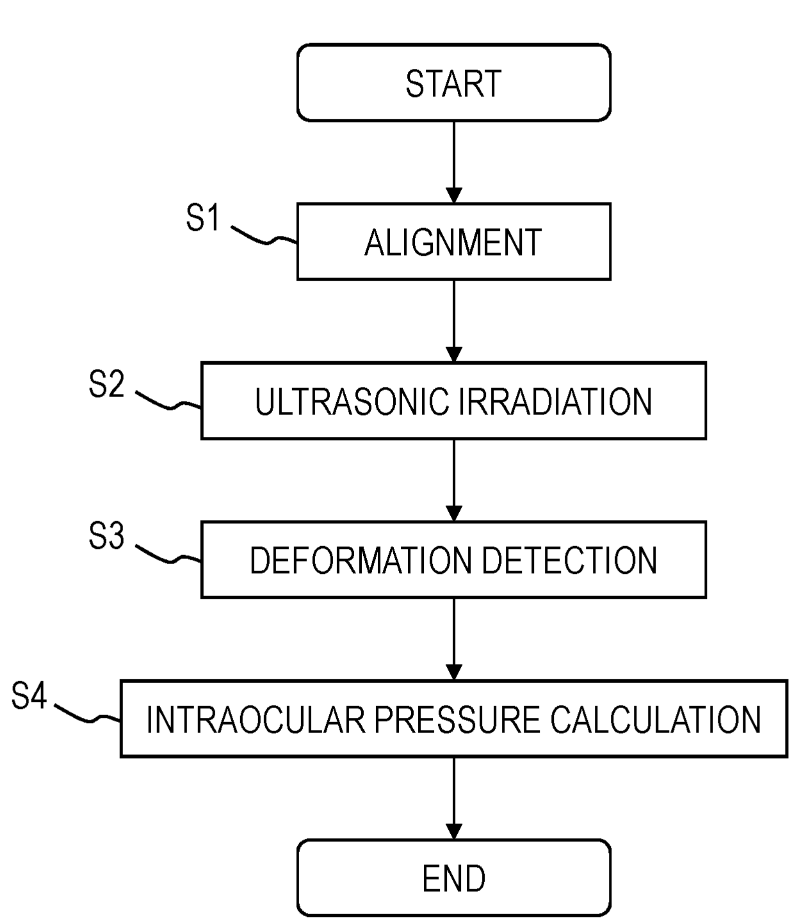
FIG. 5 is a flowchart showing a measurement operation.

A control operation for measuring intraocular pressure in the ultrasonic tonometer having the above configuration will be described with reference to FIG. 5.

(Step S1: Alignment)

Figures 6A, 6B:
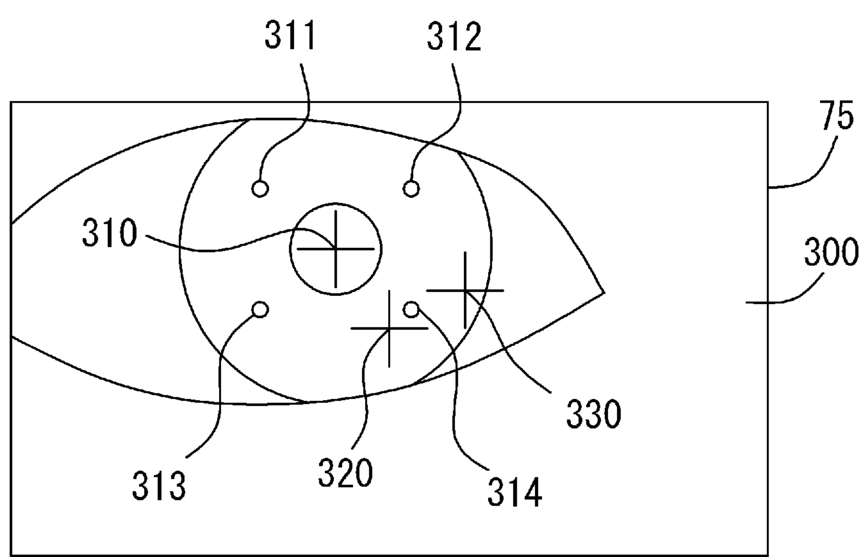
FIG. 6A is a diagram showing an example of an anterior chamber image.
FIG. 6B is a diagram showing an example of the anterior chamber image.
Figure 6C:
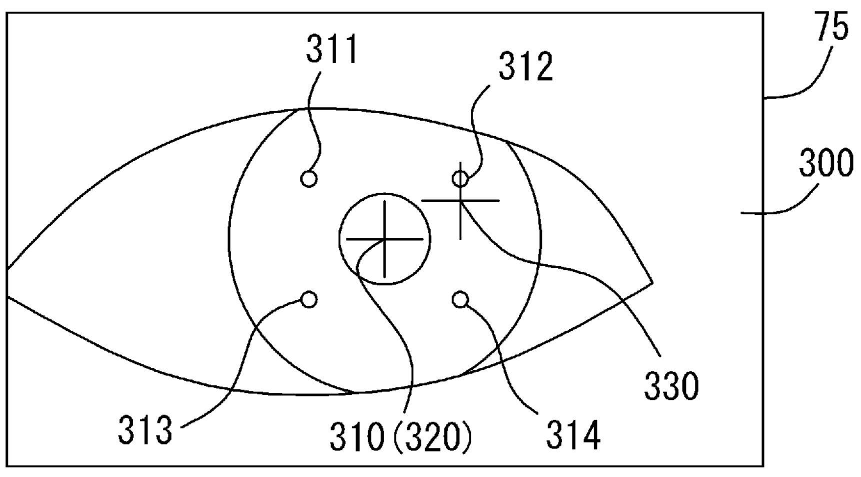
FIG. 6C is a diagram showing an example of the anterior chamber image.

First, the controller 70 is configured to align an eye of the subject whose face is supported by the face support unit 4. FIGS. 6A to 6C are examples of an anterior chamber image 300 captured by the observation system 220. In the example of FIG. 6A, alignment is incomplete. The acquired anterior chamber image 300 includes, for example, corneal reflected bright spots 311, 312, 313, and 314 due to the light from the illumination light source 241.

A cross mark 310 indicates the corneal vertex position of the subject eye calculated from the reflected bright spot of the illumination light source 241. A cross mark 320 is the optical system center (optical axis O1) of the observation system 220. A cross mark 330 indicates the sound pressure center (sound axis L1) of the ultrasonic wave output by the irradiation unit 100.

A general alignment operation is to align the corneal vertex position of the subject eye with the optical axis O1 of the observation system 220, that is, to align the position of the cross mark 310 with the position of the cross mark 320. Although there is a positional deviation between the cross mark 320 and the cross mark 330, this is due to variations in characteristics and assembly errors of the ultrasonic element 110 of the irradiation unit 100, and the positional relationship changes for each device. This deviation can be reduced by using a complicated adjustment mechanism or by matching the characteristic of the ultrasonic element 110, but it is difficult to completely eliminate the amount of the deviation.

Therefore, in the present example, the amount of deviation between the optical axis O1 (cross mark 320) and the sound axis L1 (cross mark 330) is stored in advance, and the corneal vertex is aligned with the sound axis L1 when measuring intraocular pressure. For example, the controller 70 may be configured to detect the bright spots 311, 312, 313, and 314 from the anterior chamber image acquired by the light receiving element 222 to obtain, as the corneal vertex position, the coordinates of the center of the coordinates of the four points. Then, the position of the sound axis L1 is obtained based on the position of the optical axis O1 and the amount of deviation stored in the storage unit 74, and the drive unit 5 is configured to be driven such that the position of the corneal vertex and the position of the sound axis L1 are aligned. Of course, the controller 70 may be configured to cause a display 75 to display the cross mark 310 and the cross mark 330 to guide the examiner to operate the operation unit 76 or the like to perform manual alignment. FIG. 6B shows an anterior chamber image in a case where the corneal vertex position (cross mark 310) and the sound axis L1 (cross mark 330) are aligned.

The amount of deviation between the optical axis O1 and the sound axis L1 is experimentally obtained, for example, at the time of calibration of the device, and stored in the storage unit 74. For example, measurement may be performed while shifting the position of the device by the drive unit 5 from the state where the corneal vertex position is aligned with the optical axis O1, and the position where the amount of light received by the deformation detection system 260 becomes the maximum is defined as the position of the sound axis L1 to store the amount of deviation from the optical axis O1 at that time. In addition, the position at which the sound pressure becomes the maximum may be measured by a microphone to obtain the amount of deviation from the optical axis O1.

In a case where the sound axis L1 is aligned with the corneal vertex, the optical axes O3 and O4 of the deformation detection system 260 may deviate from the corneal vertex. However, even in a case where the optical axes O3 and O4 of the deformation detection system 260 are deviated from the corneal vertex to some extent, the deformation of the cornea can be detected as long as the cornea is within a region where the cornea is deformed into a predetermined shape.

(Step S2: Ultrasonic Irradiation)

The controller 70 is configured to apply a voltage to the ultrasonic element 110 to generate an ultrasonic wave. The ultrasonic wave output from the irradiation unit 100 is applied to the subject eye, and the acoustic radiation pressure of the ultrasonic wave deforms the cornea of the subject eye.

(Step S3: Deformation Detection)

The controller 70 is configured to cause the deformation detection system 260 to detect the deformation state of the cornea. For example, the controller 70 is configured to detect that the cornea is deformed into a predetermined shape (applanation state or flattened state), based on the light receiving signal of the light receiving element 266.

(Step S4: Intraocular Pressure Calculation)

For example, the controller 70 is configured to calculate the intraocular pressure of the subject eye, based on the acoustic radiation pressure (or sound pressure) in a case where the cornea of the subject eye is deformed into a predetermined shape. The acoustic radiation pressure (or sound pressure) applied to the subject eye correlates with an irradiation time of the ultrasonic wave, and increases as the irradiation time of the ultrasonic wave is lengthened. Therefore, the controller 70 is configured to obtain the acoustic radiation pressure (or sound pressure) in a case where the cornea is deformed into a predetermined shape, based on the irradiation time of the ultrasonic wave. A relationship between the acoustic radiation pressure (or sound pressure) in a case where the cornea is deformed into the predetermined shape and the intraocular pressure of the subject eye is obtained in advance by an experiment, and is stored in the storage unit 74 or the like. The controller 70 is configured to determine the intraocular pressure of the subject eye, based on the acoustic radiation pressure (or sound pressure) in a case where the cornea is deformed into the predetermined shape and based on the relationship stored in the storage unit 74.

Of course, a method for calculating the intraocular pressure is not limited to the above-described example, and various methods may be used. For example, the controller 70 may be configured to obtain the amount of deformation of the cornea by using the deformation detection system 260, and may be configured to obtain the intraocular pressure by multiplying the amount of deformation by a conversion factor.

The controller 70 may be configured to measure the intraocular pressure, based on the ultrasonic wave reflected by the subject eye. For example, the intraocular pressure may be measured based on the changes in the characteristic of the ultrasonic wave reflected by the subject eye, or may be measured based on the amount of deformation of the cornea acquired from the ultrasonic wave reflected by the subject eye.

As described above, by aligning the corneal vertex position with the sound axis L1 based on the amount of deviation between the optical axis O1 and the sound axis L1, it is possible to appropriately irradiate the subject eye with an ultrasonic wave. As a result, the intraocular pressure can be measured while the subject eye is sufficiently deformed. In addition, it is possible to reduce the increase in the size and cost of the device, since it is not necessary to provide a complicated adjustment mechanism to reduce the deviation between the optical axis O1 and the sound axis L1, or to match the characteristic of the ultrasonic elements.

The ultrasonic tonometer 1 may include a measurement optical system configured to measure eye characteristic other than the intraocular pressure. For example, the ultrasonic tonometer 1 may include a measurement optical system configured to obtain the radius of curvature of the cornea, or a measurement optical system configured to measure eye refractive power. For example, the measurement optical system 500 may share the optical axis O1 of the observation system 220 through a beam splitter 202, as indicated by the dotted line in FIG. 2. In this case, when measuring eye characteristic other than intraocular pressure by using the measurement optical system 500, as shown in FIG. 6C, by aligning the corneal vertex (cross mark 310) with the optical axis O1 (cross mark 320), eye characteristic can be measured with high accuracy. In this manner, alignment control may be configured to be switched between the alignment based on the sound axis L1 and the alignment based on the optical axis O1 in the intraocular pressure measurement and the measurement of other eye characteristics.

In a case where the resonance frequency of the irradiation unit 100 changes due to temperature changes or the like, the position of the sound axis L1 of the irradiation unit 100 changes, and the amount of deviation between the sound axis L1 and the optical axis O1 may change. Therefore, the controller 70 may be configured to perform alignment based on the amount of deviation between the sound axis L1 and the optical axis O1 according to the resonance frequency. In this case, the amount of deviation between the sound axis L1 and the optical axis O1 corresponding to the resonance frequency may be experimentally obtained in advance, and stored in the storage unit 74.

<Z Alignment Considering Focal Position Shift>

Next, Z alignment in consideration of focal position shift of the irradiation unit 100 due to the increase in sound pressure will be described. The focal position of the ultrasonic wave applied by the irradiation unit 100 shifts farther as the sound pressure increases; that is, the focal length of the irradiation unit 100 increases. Therefore, the controller 70 may be configured to perform Z alignment in consideration of the shift of the focal position, in the alignment of step S1.

Figure 7A:
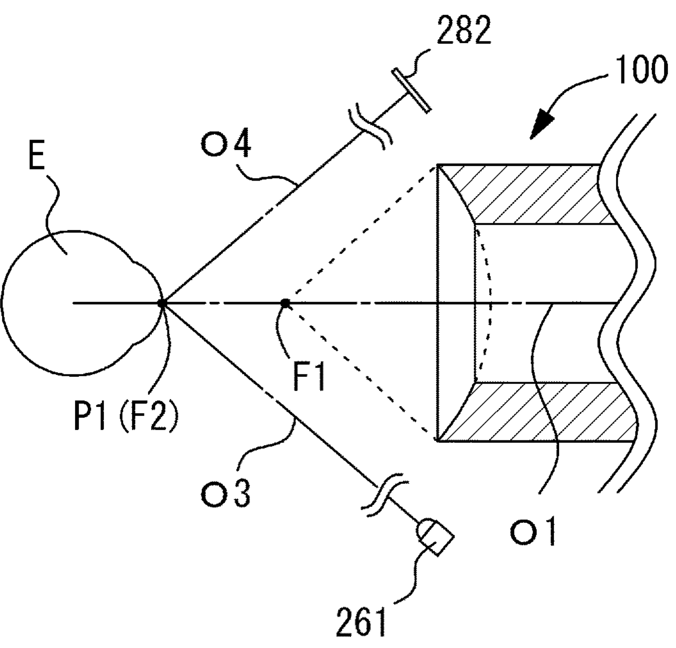
FIG. 7A is a diagram showing the positional relationship between an optical system and a position of the maximum acoustic radiation pressure.

FIG. 7A is a diagram showing the relationship between the Z-alignment detection system 280 and the position of the maximum acoustic radiation pressure. As shown in FIG. 7A, an appropriate Z-alignment position P1 detected by the Z-alignment detection system 280 is set farther than a geometric (shape) focal position F1 of the irradiation unit 100, taking into consideration the focal position shift accompanied by the increase in sound pressure. For example, the focal position F1 is the center of the radius of curvature of the end surface of the irradiation unit 100 on the side of the subject. The appropriate Z-alignment position P1 is preferably set to the position of the maximum acoustic radiation pressure (focal position after shift) F2. For example, based on the alignment information acquired by the Z-alignment detection system 280, the controller 70 is configured to control the drive unit 5 such that the position of the subject eye is aligned with the appropriate Z-alignment position P1 set farther than the focal position F1.

As described above, in the ultrasonic tonometer 1 of the present example, by aligning the subject eye with the appropriate Z-alignment position set farther than the geometric focal position of the irradiation unit 100, even in a case where the focal position shifts due to the increase in sound pressure, it is possible to appropriately irradiate the subject eye with an ultrasonic wave.

Figure 7B:
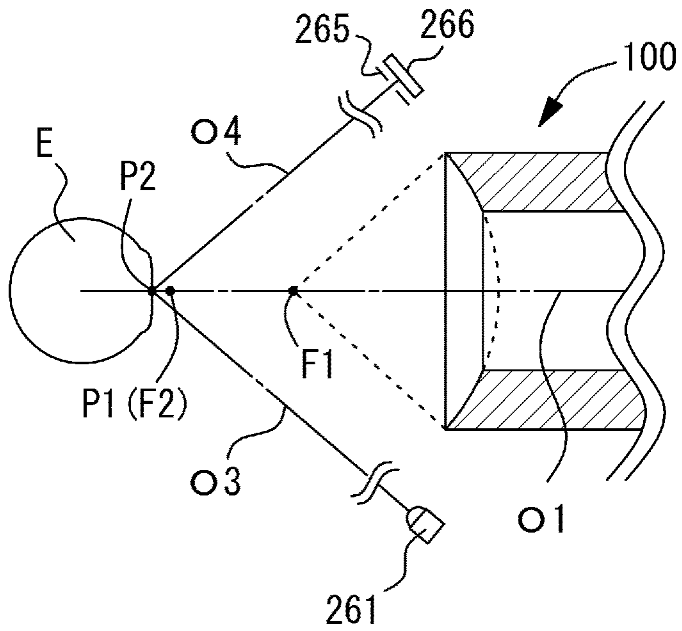
FIG. 7B is a diagram showing the positional relationship between the optical system and the position of the maximum acoustic radiation pressure.

FIG. 7B is a diagram showing the relationship between the deformation detection system 260 and the position of the maximum acoustic radiation pressure. As shown in FIG. 7B, the optical axes O3 and O4, and the intersection of the optical axes O3 and O4 of the light projecting and receiving system of the deformation detection system 260 may be disposed at a position P2 farther than the appropriate Z-alignment position P1 or the maximum acoustic radiation pressure position F2 such that the sensitivity of the deformation detection system 260 becomes the maximum in a case where the cornea is in a predetermined deformation state (for example, applanation state).

In a case where the light projecting system of the Z-alignment detection system 280 and the deformation detection system 260 are common as in the above example, the optical axis O3 of the light projecting system may be aligned with the Z-alignment detection system 280 as shown in FIG. 7A, or may be aligned with the deformation detection system 260 as shown in FIG. 7B.

The deformation detection system 260 and the Z-alignment detection system 280 are diagonally disposed in the above example, but may be disposed frontally as long as the alignment state or the deformation state of the cornea can be detected. For example, the deformation detection system 260 or the Z-alignment detection system 280 may be disposed on the optical axis O1 or on an optical axis branched from the optical axis O1.

The controller 70 may be configured to change the appropriate Z-alignment position detected by the Z-alignment detection system 280, according to the magnitude of the acoustic radiation pressure (or sound pressure). Since the acoustic radiation pressure changes depending on the magnitude of the voltage applied to the ultrasonic element 110, the application time, and the like, these parameters and the appropriate Z-alignment positions corresponding to these parameters may be stored in the storage unit 74 or the like. The controller 70 may be configured to change the appropriate Z-alignment position, according to the acoustic radiation pressure by reading from the storage unit 74 and setting the appropriate Z-alignment position corresponding to the magnitude or application time of the applied voltage. Of course, the examiner may manually adjust the setting of the appropriate Z-alignment position, according to the acoustic radiation pressure.

In a case where the resonance frequency of the irradiation unit 100 changes due to changes in temperature or the like, the focal position of the irradiation unit 100 changes, and the position of maximum acoustic radiation pressure may change. Therefore, the controller 70 may be configured to perform alignment, based on the appropriate Z-alignment position according to the resonance frequency. In this case, the appropriate Z-alignment position corresponding to the resonance frequency may be experimentally obtained in advance, and stored in the storage unit 74.

As a method for detecting the working distance, a method using an optical sensor is shown, but other sensors such as an ultrasonic sensor may be used.

In the above example, an example using a Langevin oscillator as the irradiation unit 100 has been described, but the present example is not limited thereto. The irradiation unit 100 may be configured to generate an ultrasonic wave by another method. For example, the irradiation unit 100 may be a parametric speaker in which a plurality of ultrasonic elements are disposed. The parametric speaker may be configured to focus an ultrasonic wave, for example, by disposing a plurality of ultrasonic elements on a spherical surface focused on the surface of the subject eye.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. An ultrasonic tonometer for measuring intraocular pressure of a subject eye by using an ultrasonic wave, the ultrasonic tonometer comprising:

an irradiation unit configured to irradiate the subject eye with a focused ultrasonic wave; and a Z-alignment detection unit configured to detect an alignment state in a working distance direction with respect to the subject eye, wherein an appropriate Z-alignment position is set to a position that is farther from the irradiation unit than is a geometric focal position of the irradiation unit, the appropriate Z-alignment position being detected by the Z-alignment detection unit.

2. The ultrasonic tonometer according to claim 1, further comprising:

a deformation detection unit configured to detect a deformation state of a cornea of the subject eye, wherein a detection position of the deformation detection unit is set to a position that is farther from the irradiation unit than is the appropriate Z-alignment position.

3. The ultrasonic tonometer according to claim 1, further comprising:

a controller configured to control the Z-alignment detection unit, wherein the controller is configured to change the appropriate Z-alignment position, according to a magnitude of acoustic radiation pressure or sound pressure of the focused ultrasonic wave irradiated from the irradiation unit.

4. The ultrasonic tonometer according to claim 1, further comprising:

a controller configured to control the Z-alignment detection unit, wherein the controller is configured to change the appropriate Z-alignment position, according to a resonance frequency of the irradiation unit.

5. The ultrasonic tonometer according to claim 1, further comprising:

an alignment detection unit including an imaging optical system configured to image an anterior chamber of the subject eye, the alignment detection unit being configured to detect an alignment state with respect to the subject eye, based on an anterior chamber image acquired by the imaging optical system; and a controller configured to correct alignment information acquired by the alignment detection unit, based on an amount of deviation between an optical axis of the imaging optical system and a sound axis of the irradiation unit.

6. The ultrasonic tonometer according to claim 1, wherein the irradiation unit is an ultrasonic oscillator.

7. The ultrasonic tonometer according to claim 1, wherein the irradiation unit is an Langevin oscillator.

8. The ultrasonic tonometer according to claim 1, wherein the Z-alignment detection unit is a light receiving lens and a light receiving sensor arranged to detect reflected light from the cornea to detect the alignment state in the Z direction.

9. The ultrasonic tonometer according to claim 2, wherein the deformation detection comprises a light source, a light projection lens, one or more diaphragms, a light receiving lens, and a light receiving sensor.

10. A non-transitory computer readable storage medium storing an ultrasonic tonometer control program used in an ultrasonic tonometer for measuring intraocular pressure of a subject eye by using an ultrasonic wave, the ultrasonic tonometer control program comprising instructions which, when executed by a controller, cause the ultrasonic tonometer to perform:

a Z-alignment detection step of detecting an alignment state in a working distance direction with respect to the subject eye; and a setting step of setting an appropriate Z-alignment position to a position that is farther from an irradiation unit than is a geometric focal position of the irradiation unit, the irradiation unit being configured to irradiate the subject eye with a focused ultrasonic wave, the appropriate Z-alignment position being detected in the Z-alignment detection step.

11. An ultrasonic tonometer for measuring intraocular pressure of a subject eye by using an ultrasonic wave, the ultrasonic tonometer comprising:

an irradiation unit configured to irradiate the subject eye with an ultrasonic wave;

an alignment detection unit including an imaging optical system configured to image an anterior chamber of the subject eye, the alignment detection unit being configured to detect an alignment state with respect to the subject eye, based on an anterior chamber image acquired by the imaging optical system; and a controller configured to correct alignment information acquired by the alignment detection unit, based on an amount of deviation between an optical axis of the imaging optical system and a sound axis of the irradiation unit.

12. The ultrasonic tonometer according to claim 11, further comprising:

a measurement optical system that shares the optical axis with the imaging optical system, and the measurement optical system being configured to measure an eye characteristic different from the intraocular pressure, wherein the controller is configured to switch whether or not to correct the alignment information in measurement of the eye characteristic by the measurement optical system and in measurement of the intraocular pressure by the irradiation unit.

13. The ultrasonic tonometer according to claim 11, further comprising:

a drive unit configured to move the irradiation unit, wherein the controller is configured to control the drive unit based on the alignment information corrected by the controller to perform alignment of the irradiation unit with respect to the subject eye.

14. The ultrasonic tonometer according to claim 11, wherein the controller is configured to cause a display to display the alignment information corrected by the controller.

15. The ultrasonic tonometer according to claim 11, wherein the controller is configured to correct the alignment information, according to a resonance frequency of the irradiation unit.

16. The ultrasonic tonometer according to claim 11, further comprising:

a Z-alignment detection unit configured to detect an alignment state in a working distance direction with respect to the subject eye, wherein an appropriate Z-alignment position is set to a position that is farther from the irradiation unit than is a geometric focal position of the irradiation unit, the appropriate Z-alignment position being detected by the Z-alignment detection unit.

17. The ultrasonic tonometer according to claim 11, wherein the irradiation unit is an ultrasonic oscillator.

18. The ultrasonic tonometer according to claim 11, wherein the controller is configured to correct the alignment information based on the amount of deviation according to a change in a resonance frequency of the irradiation unit.

19. The ultrasonic tonometer according to claim 16, wherein the Z-alignment detection unit is a light receiving lens and a light receiving sensor arranged to detect reflected light from the cornea to detect the alignment state in the Z direction.

20. The ultrasonic tonometer according to claim 11, wherein the optical system of the alignment detection unit comprises one or more of an objective system, an observation system, a fixation target projection system, a deformation detection system, a dichroic mirror, and a beam splitter.

21. The ultrasonic tonometer according to claim 19, wherein the optical system comprises the objective system, the observation system, the fixation target projection system, the deformation detection system, the dichroic mirror, and the beam splitter.

22. A non-transitory computer readable storage medium storing an ultrasonic tonometer control program used in an ultrasonic tonometer for measuring intraocular pressure of a subject eye by using an ultrasonic wave, the ultrasonic tonometer control program comprising instructions which, when executed by a controller of the ultrasonic tonometer, cause the ultrasonic tonometer to perform:

an alignment detection step of detecting an alignment state with respect to the subject eye, based on an anterior chamber image acquired by an imaging optical system configured to image an anterior chamber of the subject eye; and a correction step of correcting alignment information acquired in the alignment detection step, based on an amount of deviation between an optical axis of the imaging optical system and a sound axis of an irradiation unit.

* * * * *